United States Patent [19]

Urso

[11] Patent Number: 4,898,148
[45] Date of Patent: Feb. 6, 1990

[54] VERSATILE HEATER/COOLER

[76] Inventor: Charles L. Urso, 215 Newton St., Waltham, Mass.

[21] Appl. No.: 212,505

[22] Filed: Jun. 28, 1988

[51] Int. Cl.$^4$ .............................................. A61F 7/00
[52] U.S. Cl. ..................................... 126/204; 126/266; 126/367; 126/208; 126/402
[58] Field of Search ...................... 126/5, 43, 44, 204, 126/208, 210, 206, 266, 367, 389; 128/399, 400, 402; 312/1

[56] References Cited

U.S. PATENT DOCUMENTS

| | | | |
|---|---|---|---|
| 506,810 | 10/1893 | Cardarelli | 126/367 |
| 971,735 | 10/1910 | Edwards | 126/266 |
| 1,468,561 | 9/1923 | Friend | 126/367 |
| 1,754,971 | 4/1930 | Waigand | 128/402 |
| 3,220,424 | 11/1965 | Nelson | 128/402 |
| 3,811,559 | 5/1974 | Carter | 126/266 |
| 4,329,997 | 5/1982 | de Yampert et al. | 128/402 |
| 4,331,254 | 5/1982 | Haggerty | 312/1 |
| 4,497,313 | 2/1985 | Kurosawa | 128/400 |
| 4,691,688 | 9/1987 | Urso | 126/204 |

FOREIGN PATENT DOCUMENTS 2613 of 1909 United Kingdom ................. 126/367

OTHER PUBLICATIONS

Charles L. Urso patent application Ser. No. 07/194,837 filed May 17, 1988 entitled "Versatile Heater for Under-Blanket Heating, Tent Heating, and Food Heating".

Primary Examiner—James C. Yeung
Attorney, Agent, or Firm—Hamilton, Brook, Smith & Reynolds

[57] ABSTRACT

A versatile heater/cooler (2) comprising a chest (4) having insulated walls (6, 8, 10, 12, 14) including a lid (10). Contained within the chest is a removable heating and cooling source (46) which is submersible in a liquid for heating or cooling the latter. The source comprises first and second vertical conduits (48, 50) having lower portions connected for fluid communication with a transverse body (52) which forms a combustion chamber. The chamber serves for burning fuel (80) or for containing a refrigerant introduced by way of the conduits. Included in the chest lid is a vent port (110) for venting the chest contents including the source, and two limb ports (18, 20) for inserting the limbs of a user through the ports and into the interior of the chest. A self-adjusting shield (22, 24) connected to an edge portion of each limb port, yieldingly surrounds each limb for preventing hot or cold air losses from the chest. The invention also includes movable carrying handles (126, 128) which, in an erect position, form a frame which supports various user aids for special applications of the invention.

32 Claims, 6 Drawing Sheets

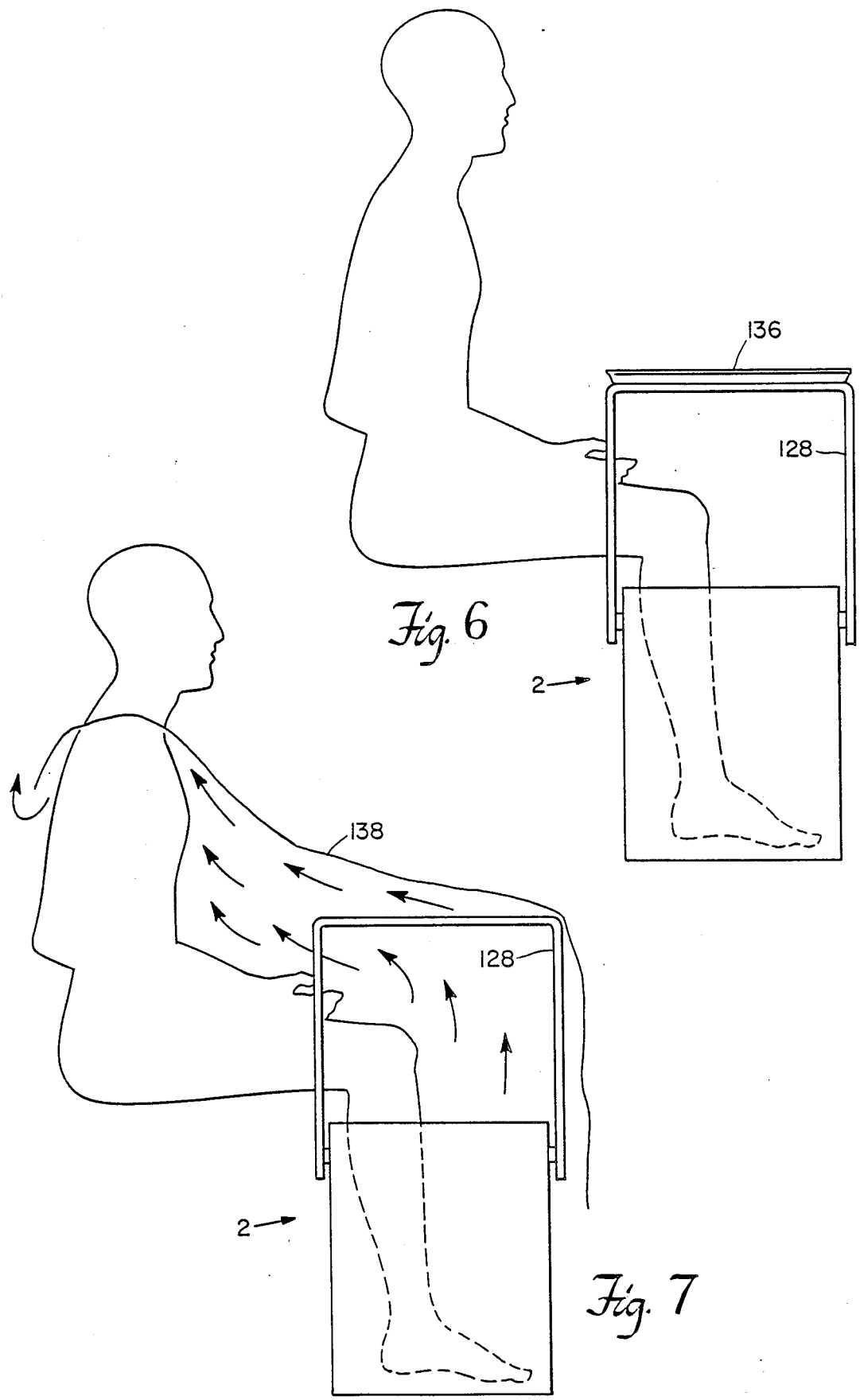

VERSATILE HEATER/COOLER

TECHNICAL FIELD

This invention relates to insulated enclosures for maintaining a temperature condition and more particularly to insulated enclosures having self-contained submersible heating means.

BACKGROUND

When we leave the comforts of home to experience the great outdoors, we leave the important benefits of home fixtures and appliances. Among the most needed of the home devices are those that maintain water at high and low temperatures and those that contain the desired water for its various uses. This may involve a water heater, a refrigerator, a sink and a tub. To bring along existing portable substitutes for such devices is impractical since together they would constitute too large a load for most family cars.

Dish Washing and Bathing

Portable means for dish washing and for personal bathing often requires a multi-gallon pot, a portable stove, and a plastic tub; a bulky combination. A more compact combination is needed.

First Aid

The fast application of wet heat or cold is useful in the treatment of some types of injuries which are apt to occur in outdoor environments. Conventional portable devices for providing the treatment would include an insulated cooler, a large pot, a portable stove, and a large basin or pan. An all-in-one combination would be a great benefit.

Heating and Cooling the Body

Because of poor blood circulation, elderly people are in need of a means for heating or cooling their bodies when outdoor temperatures are insufficient or excessive. Small children are also very vulnerable to discomfort and injury from temperature extremes. A convenient portable combination heater and cooler is needed for heating or cooling a person's body to help avoid heat stroke, heat exhaustion, hyperthermy, hypothermy, and frostbite. Such an apparatus could serve as a "safety net" for the elderly and children in changing weather conditions. Others who could benefit are fishermen, miners, farm workers, construction workers, campers, boat operators, athletes, and other sportsmen.

Heating Food

Heating food when there is no kitchen is available, especially food in quantity, generally requires bulky equipment including a portable stove or heater and large pots or pans.

It would be highly desirable, therefore, to provide a versatile heater/cooler that could be safely used for all of the above-mentioned needs, including dish washing, bathing, first aid treatments, body heating and cooling, and food heating and cooling.

OBJECTS AND ADVANTAGES

Objects and advantages of the invention are:

to provide a compact apparatus for washing dishes, utensils and other camping equipment wherein the apparatus includes a self-contained submersible heating device to heat water in a tub-like receptacle for immersing the articles to be washed;

to provide a compact apparatus for personal bathing having the features described above wherein a user can stand in the tub-like receptacle;

to provide a compact apparatus for cooling food or heating food in sufficient quantity to be suitable for catering, especially in conditions where there is minimal equipment and no kitchen;

to provide a compact apparatus for first aid and other medical applications having means for keeping water hot or cold, and including a receptacle for treating some types of injuries and afflictions to limbs; and to provide a compact apparatus for heating or cooling the body of the user.

Other objects and advantages will become apparent from consideration of the drawings and ensuing description which includes a list of more specific uses and applications.

BRIEF DESCRIPTION OF THE DRAWINGS

The accompanying drawings in combination with the description herewith, illustrate features and advantages of the invention. Like reference characters in different views refer to the same parts. The drawings are intended to illustrate principles of the invention and are not necessarily to scale and in which drawings:

FIG. 6 is a diagrammatic view of a seated user having at least one leg inserted through a limb port and into the chest, wherein the carrying handles are in an upright position for supporting a tray;

FIG. 7 is a diagrammatic view of a seated user having his legs inserted into the chest wherein a blanket covers the user and forms a canopy over the upright carrying handles to entrap heated air rising from the vent port thereby enveloping the user;

DETAILED DESCRIPTION

Figure 1:
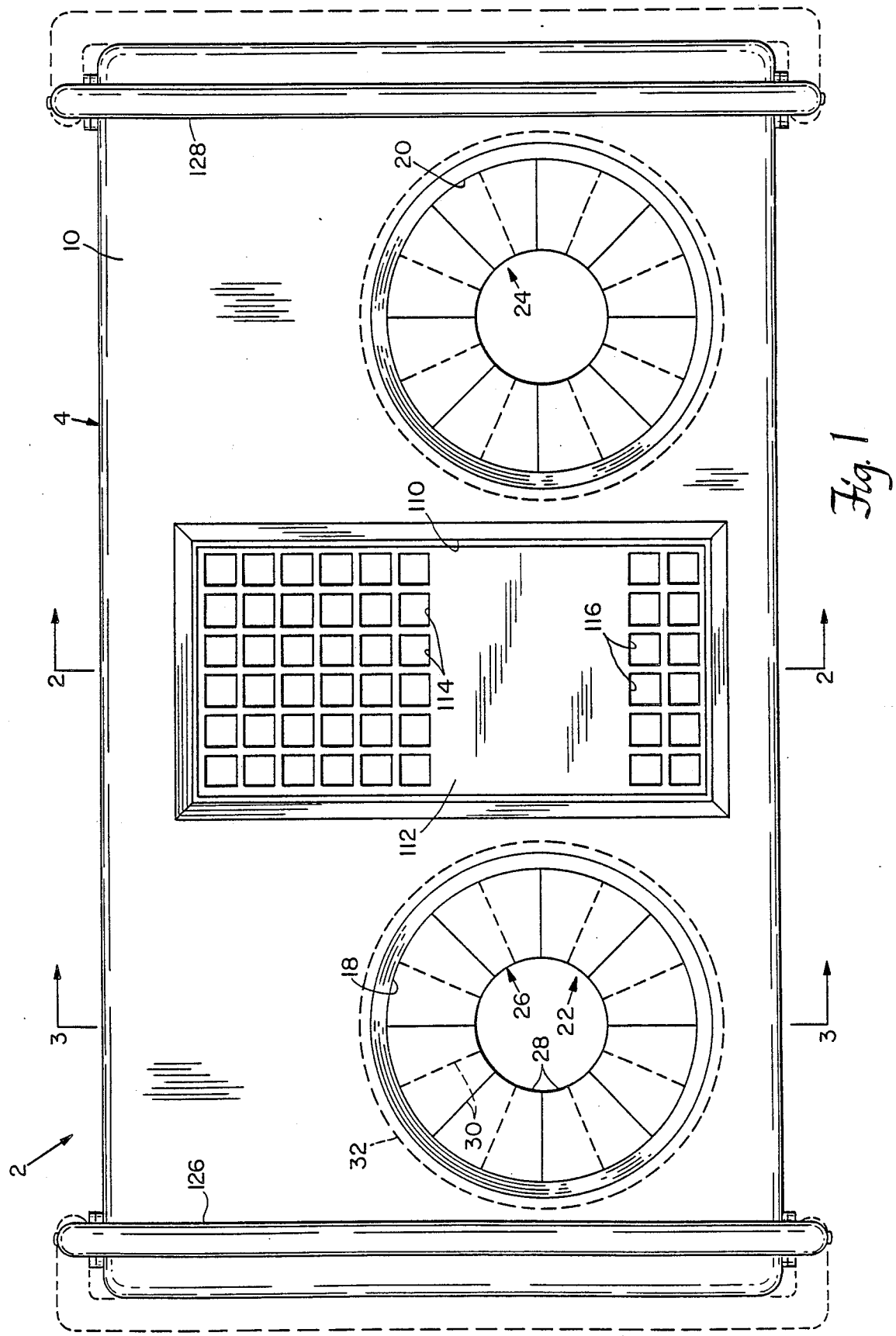
FIG. 1 is a top view of an apparatus in accordance with the invention in proper orientation for limb insertion wherein the limb port covers are removed and the vent port cover is removed.

A preferred embodiment of the invention which can serve as either a heater or cooler (referred to herein as a versatile heater/cooler) is indicated generally by reference numeral 2 in FIG. 1. The invention comprises a six-sided container or chest 4 (FIG. 1 and 2) having walls 6, 8, 10, 12, 14 defining a hollow interior. The walls include conventional insulating means for inhibiting heat transfer through the walls. Details of the internal construction of the walls are generally not shown since the construction methods are well-known in the art. A conventional double-wall construction may be used, for example, wherein the inner wall element may be aluminum or a plastic sufficiently heat resistant to contain hot water in the chest. Each of the chest walls may otherwise be of a single-wall construction comprising a rigid, heat resistant, foam plastic. The minute cells in the foam provide the insulating quality.

Wall 10 serves as a removable lid which includes edge portions defining limb ports 18, 20 (FIG. 1). The port size is suitable for insertion of a limb through each port and into the interior of the chest (FIG. 6 and 7). Alignment of the two ports is parallel with the longitudinal axis of the lid so that two limbs of a user can conveniently be simultaneously inserted in the chest. Hence, a seated user can insert both lower legs into the chest, one leg in each respective port. The edge portion of each port being curved or annular to comfortably surround the limb.

Figure 3:
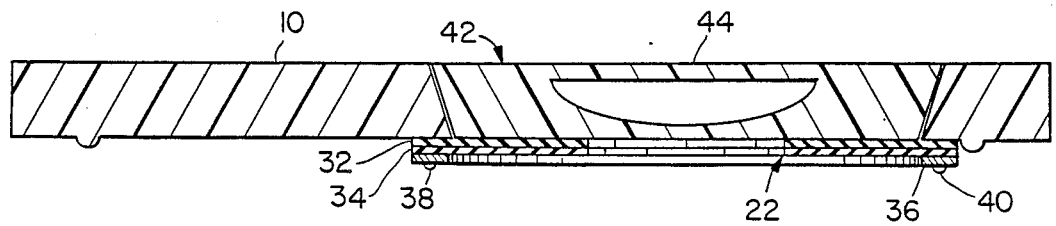
FIG. 3 is a cross-sectional view of the chest lid taken along the line 3—3 of FIG. 1, but including a limb port cover.

Connected to an underside of each port edge portion is a self-adjusting shield 22, 24, respectively, such that each shield is concentric with a port (FIG. 1 and 3). Referring to shield 22, the same includes a corolla 26 having a plurality of resilient petals 28. The petals are formed by equidistant radial cuts 30 through each of two doughnut-shaped rubber sheets 32, 34, one sheet lying over the other. Each radial cut begins at the aperture or inside edge of a sheet and extends radially outward to end just below the edge of port 18. Each sheet is larger in diameter than a port diameter so that each petal includes an outer portion attached to a peripheral portion of a sheet. The cuts in sheet 32 (indicated by solid lines in FIG. 1) are located approximately midway between the cuts in sheet 34 (indicated by broken lines). Hence, the corolla petals overlap each other to resist the formation of open spaces between adjacent petals as they bend and spread.

Shield 22 is sandwiched between the edge portion of port 18 and an aluminum ring 36 fastened to the lid 10 by rivets 38, 40. The rivets pass through the ring and the shield, thereby connecting the shield to the port edge portion.

Shield 24 is constructed and mounted in the same manner as shield 22. The corolla petals of a shield are positioned to surround a limb passing through the associated port such that the petals yieldingly contact the limb thereby resisting the passage of air through the port. Thus, by minimizing any exchange of air between the interior and the exterior of the chest 4, the shields help to preserve a temperature condition in the interior of the chest.

When limb port 18 is not in use, it is closed by a removable limb port cover 42 (FIG. 3) which includes a handle 44 positioned in an annular recess in the cover. The cover is insulated and closely fitted to the port to avoid heat transfer through the idle port. A similar cover (not shown) closes port 20 when the latter is not in use.

Figure 2:
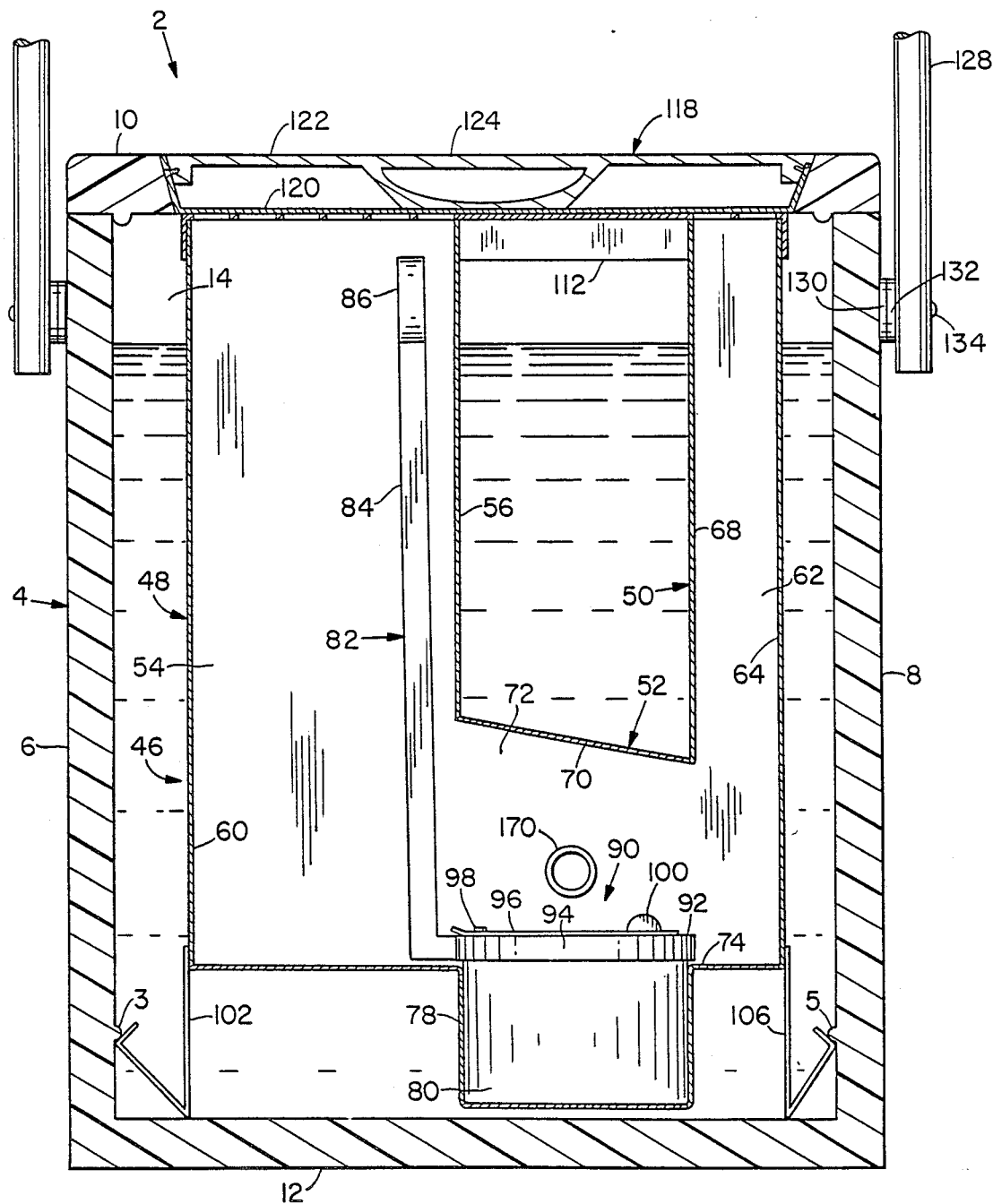
FIG. 2 is a cross-sectional view taken along the line 2—2 of FIG. 1, but including the vent port cover.
Figure 4:
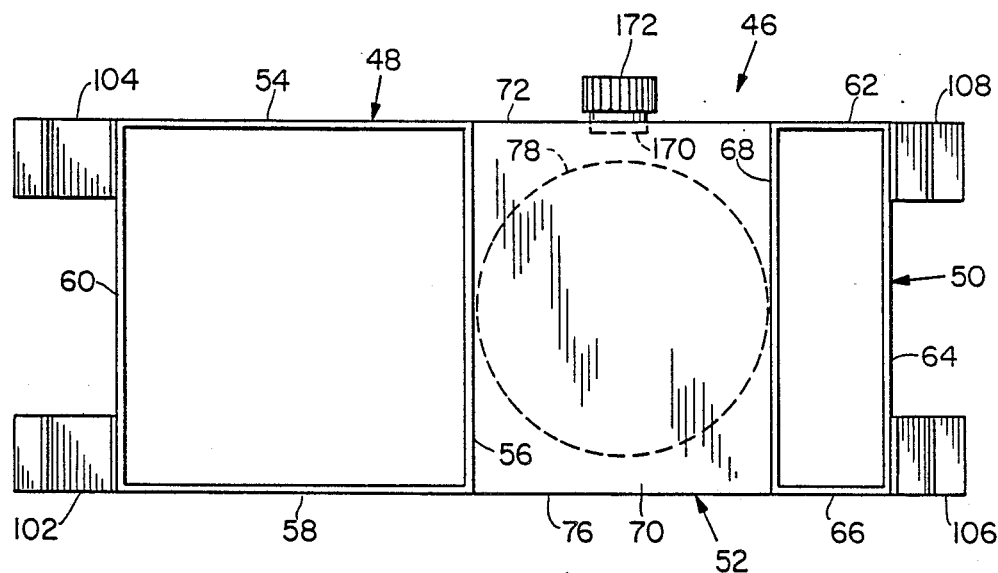
FIG. 4 is an isolated top view of the submersible heating and cooling source without the grate cap.

Within the chest 4 is a submersible heating and cooling source or H/C source 46 (FIG. 2 and 4). The H/C source comprises a first conduit 48 normally positioned vertically. Conduit 48 includes upper and lower portions wherein the upper portion is open for fluid communication between the hollow interior of the conduit and the outside atmosphere. Also included is a second conduit 50 normally positioned vertically. Conduit 50 includes upper and lower portions wherein the upper portion is open for fluid communication between the hollow interior of the conduit and the outside atmosphere.

A transverse body 52 forms a combustion chamber and is connected with the lower portion of the first conduit 48 wherein the combination forms a first conduit passage. Thus, allowing fluid communication between the chamber and the first conduit interior. The body 52 is also connected with the lower portion of the second conduit 50 wherein the combination forms a second conduit passage. Thus, allowing fluid communication between the chamber and the second conduit interior. The combination also allows the conduit interiors to be in fluid communication with each other.

As shown in the figures, conduit 48 includes vertical walls 54, 56, 58, and 60. Conduit 50 includes vertical walls 62, 64, 66, and 68. Transverse body 52 includes a sloped wall or roof 70, a horizontal wall or floor 74, and vertical walls 72, 76.

As can be seen in FIG. 2, the first conduit passage (formed at the joint of body 52 with conduit 48) is relatively higher than the second conduit passage (formed at the joint of body 52 with conduit 50). Hence, the first conduit 48 receives rising combustion gases from the combustion chamber and thereby functions as a flue wherein the second conduit 50 functions to conduct air into the chamber.

The combination including the conduits and the chamber may be constructed from sheet metal by ordinary shop methods.

Though the conduits and combustion chamber as described have square or rectangular cross-sections, each may alternatively be formed from a single curved wall so as to have a circular or other closed loop cross-section.

Extending downwardly from the body 52 is a cup-shaped fuel well 78. Access to the interior of the well 78 is through an annular entry in floor 74. Thus, the well is in fluid communication with the conduits 48, 50.

Received in the fuel well is a close-fitting can 80 containing semi-solid fuel of the type commonly used in portable stoves and for heating chafing dishes. The commercially available seven ounce can is preferred.

The close fit between the fuel can 80 and the well 78 results in the transfer of heat from the fuel to a liquid in which the H/C source is immersed during operation. This promotes an even burn rate of the fuel.

Figure 5:
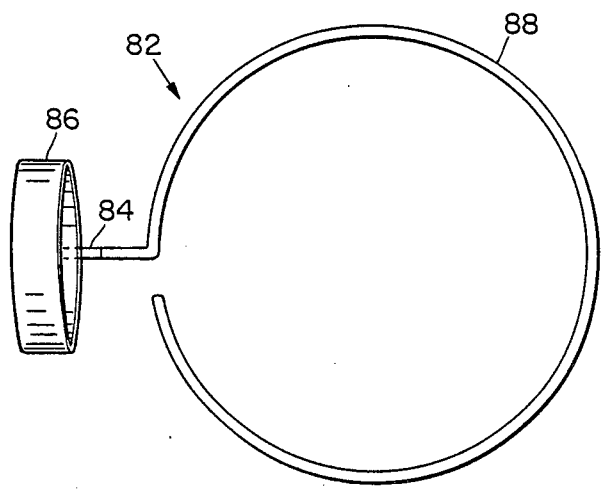
FIG. 5 is an enlarged top view of the fuel holding arm.

Fuel can 80 is placed and removed in the well 78 by means of a fuel holding arm 82 (FIG. 2 and 5). Arm 82 comprises an L-shaped shaft 84 having an upper end portion connected to a ring-shaped handle 86. Shaft 84 also includes a lower end portion which is connected to a ring-shaped holder 88 for surrounding and holding the fuel can 80. The holder 88 is sufficiently resilient so as to embrace the can under spring tension. A protruding annular top edge of the can prevents the latter from sliding through the holder. The fuel holding arm 82 can be formed by bending a single strip of metal into the described shape.

By holding the handle 86, a user can pass the arm 82 and fuel can 80 through the first conduit 48 for placement or removal of the can. The inner corners of conduit 48 provide ample room for arm 82 as the fuel can is lowered or raised in the conduit. Arm 82 remains in the H/C source 46 during operation of the latter.

If preferred, chamber floor 74 may have a concave shape to make it easier to guide fuel can 80 into the fuel well 78.

Positioned over the fuel can 80 and around the holder 88 is a flame attenuator 90. The attenuator 90 includes a cap portion 92 which resembles the lid of a jar. Cap 92 covers the fuel can while a rim portion 94 of the cap encircles the holder 88. A vertical slot (not shown) in the rim 94 receives the lower end portion of the shaft 84 so that the cap is able fit around the holder. The cap 92 includes a central annular aperture (not shown) through which a flame from the fuel can 80 passes through the attenuator. Also included is an annular plate 96 pivotally connected to the cap by a rivet 98. The plate is larger in diameter than the cap aperture and includes a small handle 100 so that a user can slide the plate over the aperture. Thus, the plate can be used to control the flame size by adjusting the amount by which the cap aperture is covered by the plate. The attenuator operates in a manner similar to conventional flame attenuators for other uses of semi-solid fuel, such as under chafing dishes.

Referring to FIG. 2 and 4, wall 72 of the transverse body 52 includes an aperture which receives a short pipe nipple 170. The nipple is press-fitted or welded therein to define a lighting port for igniting the fuel. A match can be passed through the lighting port to ignite the fuel.

The portion of the nipple 170 protruding from the outside of the wall 72 is threaded to mate with a threaded lighting port cap 172. By screwing the cap 172 over the nipple, the cap forms a fluid tight seal over the port.

All joints connecting the combination, which includes the conduits 48, 50, transverse body 52 and fuel well 78, are welded or brazed so that the combination below the conduit openings is fluid tight.

Welded to lower corners of the H/C source 46 are four resilient anchoring legs 102, 104, 106, and 108. Each leg is formed from a strip of resilient metal. When the H/C source is placed in the chest 4, a distal portion of each leg snaps under a horizontal bead 3, 5 (FIG. 2) protruding from a respective chest wall 6, 8. This arrangement provides legs for the H/C source and means for holding the latter down when the chest is filled with water or other liquid. Hence, the H/C source is prevented from floating. A user removes the H/C source from the chest by pulling the device up, thereby overcoming the spring resistance of the legs which can snap over the beads in either direction (up or down). Guides (not shown) on the chest walls can be used to guide the H/C source to a central portion of the chest interior.

The lid 10 includes a centrally positioned vent port 110 which is a rectangular opening directly above the H/C source 46 for ventilation of the latter (FIG. 1). A perforated grate cap 112 is placed over the openings of both conduits to prevent small objects from falling into the H/C source. Perforations 114 are positioned over the first conduit opening while perforations 116 are positioned over the second conduit opening (FIG. 1 and 2).

The lid 10 also includes a vent port cover 118 (FIG. 2) comprising a shallow rectangular metal pan 120 having a bottom wall and four side walls arranged to fit tightly into the vent port. The pan side walls are fixed to a molded plastic upper portion 122 of the cover 118 by means of screws. A handle 124 is positioned in an annular recessed portion of the molded plastic. Thus, the vent cover 118 is double-walled with an insulating void therebetween.

Referring to FIG. 2, the metal portion of cover 118 meets flush with grate cap 112 so that all the grate perforations are completely covered. It can be seen, therefore, that vent cover 118 can serve to shut off the H/C source. That is, the H/C source can only operate when the vent cover is removed, since placement of the cover 118 in the vent port completely prevents any gases from entering or leaving the H/C source. The vent cover also serves to prevent the semi-solid fuel from drying out when the fuel can cover is removed. Hence, when the vent cover is in place, the fuel will not evaporate. Of course, the vent cover also helps to keep the contents of the chest hot or cold.

The heater/cooler 2 includes a U-shaped carrying handle 126, 128 pivotally mounted at each end portion of the chest (FIG. 1, 2, 6 and 7). Tightly sandwiched between each handle leg and a chest wall, is a spacer 130 (FIG. 2) juxtaposed with a rubber washer 132. A rivet 134 passes through the handle leg, the washer and spacer, and into the chest wall 8 to pivotally connect the combination. Friction, resulting from the tightly compressed rubber washer associated with each handle leg, maintains the handles in the position in which they are placed by a user. The handles may be moved, however, between an upper or erect position (indicated by the solid line representation in FIG. 1) and a lower position (indicated by the broken line representation) clear of the lid 10. Various uses of the handles will be explained in other sections of this specification.

A conventional drain plug (not shown) may be included in the chest for draining the latter of water or other liquid.

The chest lid 10 may also include means for holding the vent port cover and limb port covers in place in the lid. Hence, the lid could be removed and placed in any position without losing the port covers. Conventional latches may be used, but a very convenient port cover holding means is described in the alternative embodiments section of this specification.

Operation of the Submersible H/C Source

Grate cap 112 is first removed in order to place a fuel can in the H/C source. By using arm 82, the fuel and the attenuator are positioned in the fuel well as shown in FIG. 2. As mentioned, the inside corners of first conduit 48 provide ample room for the arm as the latter is lowered into the conduit. Grate cap 112 can then be replaced on the H/C source wherein the lighting port cap 172 can be removed and the fuel ignited by way of the lighting port. After the fuel is ignited, the lighting port cap can be replaced and the H/C source can be immersed in liquid contained by the chest 4.

Alternatively, the fuel may be ignited outside of the H/C source while being held with a fuel holding arm. In that case, a preferred arm is the alternative fuel holding arm 174 shown in FIG. 10 and 11. Arm 174 includes added safety features described in the Alternative Embodiments section of this specification. With the use of arm 174, the ignited fuel may be placed in the fuel well as described above. An advantage of the latter method of igniting the fuel, is that the H/C source does not have to be removed from the chest.

The flame heats roof 70 and other walls of the H/C source to transfer heat to the water or other liquid in which the H/C source is immersed. Heat from the fuel is transferred through the well to the water, thereby allowing an even burn rate.

The roof 70 of the combustion chamber is sloped upwardly to direct rising combustion gases to the first conduit 48 so that the latter functions as a flue. Second conduit 50 functions to conduct atmospheric air to the chamber for supporting combustion.

With the flame source being well protected in the H/C source and chest, the operating heat/cooler can be left unattended to heat water and/or food in the chest. Users are free to enjoy outdoor activities.

The described combination provides a highly efficient system for heating a large volume of liquid, since there is very little heat loss. As mentioned, the H/C source can be shut off by replacing the vent port cover 118. The cover extinguishes the flame and prevents evaporation of the semi-solid fuel. It also keeps the heated liquid hot.

H/C source 46 also functions to contain a refrigerant, such as dry ice or ice cubes, introduced by way of the conduits so that the contents of the insulated chest 4 can be kept cold. Filling the H/C source with water and freezing it is another method of providing a refrigerant.

SPECIFIC USES OF THE INVENTION

For Dish Washing

After heating water in the chest 4 as described above, the lid 10 and H/C source 46 may be removed so that the open chest can serve as a water-filled tub or sink. Dishes, pots, pans, and other equipment may be immersed in the chest for washing at campsites and other remote locations.

For Bathing

Just as for dish washing described above, the open chest with its hot water can be used as a sink for personal washing. A user can also stand in the chest while taking a sponge bath. A child could sit in the chest water and thus use it as a tub.

For Heating or Cooling Food

With water contained in the chest, food contained in crocks, jars, cans and pots can be immersed in the chest water in order to heat the food. Lid 10 is kept closed during the heating process. The hot water can later be used for washing.

Instead of water, the chest can be filled with "uncontained" soup or chowder wherein the chest serves as the container. The H/C source 46 can then be immersed in the soup or chowder for heating. In this manner, other liquid foods including those having suspended solids can be heated. For these applications the submersible H/C source and the inner walls of the chest can be made from nontoxic metal, such as aluminum or stainless steel.

Hence, the invention is ideal for catering clambakes and outings with minimal equipment. The H/C source 46 can be in operation while on route to a function so that hot food can be served upon arrival. A low flame setting, in concert with the insulated chest, can keep food hot all day in the case of a full-day outing.

For cooling food or drinks in the chest, the H/C source 46 can be filled with a refrigerant as described above.

Heating and Cooling the Body

Blood continuously circulates through the skin of each limb wherein a considerable amount of heat is exchanged with the exterior environment. The same blood that passes through the limbs also travels throughout all the body vessels in continuous cycles. Therefore, if limbs are immersed in hot or cold water in the heater/cooler, the whole body will receive or lose heat (depending on whether the water temperature is above or below normal body temperature).

Hence, by having cold water in the chest 4 and both legs in the limb ports, an overheated person will cool his entire body. He could be seated in the same manner as the person indicated in FIG. 6. The heater/cooler would be very useful, for example, at outdoor events for the elderly or at athletic events. The invention can help avoid heat stroke or heat exhaustion.

As mentioned, hot water in the chest 4 can keep a user's entire body warm. A user will not burn his feet by contact with the operating H/C source because the water absorbs the heat. However, if the water becomes too warm the H/C source can be shut off or removed from the chest. Referring to FIG. 7, a sitting user can also cover himself and the upright handles with a blanket 138. The handles form a canopy frame wherein the blanket becomes a canopy for entrapping heated air (indicated by arrows) from the vent port (the vent port cover is removed). The heated air envelops the user for additional warmth. For added safety, the H/C source 46 could be shut off or removed after the water is heated. The hot air under the blanket would then be derived from the hot water.

The invention would be advantageous, therefore, in an emergency or simply as a means to keep warm or cool.

In the above applications of the invention, the user can wear disposable plastic coverings (such as those used by hospital personal) over his legs to avoid getting wet. This can also be done in some of the medical uses of the heater/cooler.

For First Aid and Other Medical Uses

When the H/C source 46 is filled with ice cubes, water in the chest can be kept cold. Alternatively, with the H/C source burning fuel, the chest water can be kept hot as long as desired. Thus, wet cold or wet heat treatments can be provided by inserting one or two arms or legs through the limb ports. Medications can be added to the water when appropriate.

Immersion, rather than wet pad applications, is preferred in some types of injuries or afflictions to a limb. The buoyancy of the water provides support and relieves stress and tension on the muscles and joint. The self-adjusting shields 22, 24 help to maintain the insulating efficiency of the chest. Thus, repeated treatments can be given with a minimal or limited amount of ice or fuel.

First aid, requiring wet heat or cold, can be provided by using the invention at construction sites, campsites, and remote locations. Paramedics can start treatments with the invention while on route to a hospital in cases involving burns, frostbite, swelling injuries, and some types of animal bites and stings. Visiting nurses and physical therapists can train home users to give self-treatments with the invention. Nursing homes, rehabilitation hospitals and other institutions could use the heater/cooler to treat patients in recreational settings including porches, patios, picnics and outings.

FIG. 6 indicates the position of a patient receiving a treatment of a lower leg. The opposite leg (not shown) can extend out over the top of the chest 4, resting on the chest lid. An arthritic patient might have both legs in the chest for treatment. The carrying handles are in an upright position for conveniently supporting a dinner tray 136 or table top. Thus, the patient can have dinner, write, or do other table activities.

Arms can be treated by placing the heater/cooler on a chair and inserting the arms through the limb ports.

In another application, the heater/cooler can be placed on a chair with the handles 126, 128 placed in the upright position. A large towel can then be supported over the handles to form a tent. A sitting patient can use the tent for inhalation treatments that require hot moist air (the vent port cover 118 and H/C source 46 are removed before the treatment). Medication that is appropriate for the ailment can be added to hot water in the chest 4. In this application, the water can be heated by conventional methods (when available) for expediency.

ALTERNATIVE EMBODIMENTS OF THE INVENTION

Figure 8:
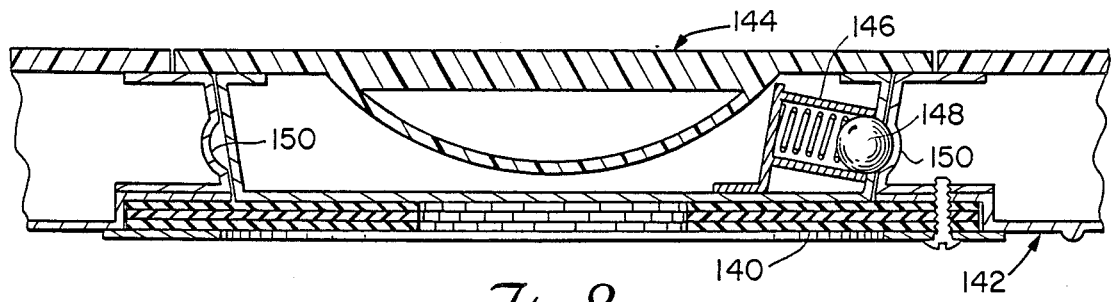
FIG. 8 is a fragmentary cross-sectional view of an alternative embodiment of a lid having a limb port, a limb port cover and a latch.

Shown in FIG. 8 is a self-adjusting shield 140 having three layers of corolla petals rather than two. The shield 140 is housed in an annular recess within the double-walled chest lid 142. Housed within a limb port cover 144, is a latch comprising a cylinder 146 enclosing a helical compression spring. The spring urges a ball 148 against an aperture in a peripheral wall of the cover 144. Thus, a portion of the ball protrudes through the aperture.

A peripheral portion of the lid 142 surrounding a limb port includes a groove 150 for receiving the ball 148 when the cover 144 is placed in the lid. Two similar latches (not shown) are also housed in the cover 144 so that the three latches are equidistant from each other in a triangular arrangement. Hence, the cover 144 remains in the lid 142 even when the latter is turned upside-down. The latches will yield, however, when the cover 144 is pulled out of the lid by a user.

Figure 9:
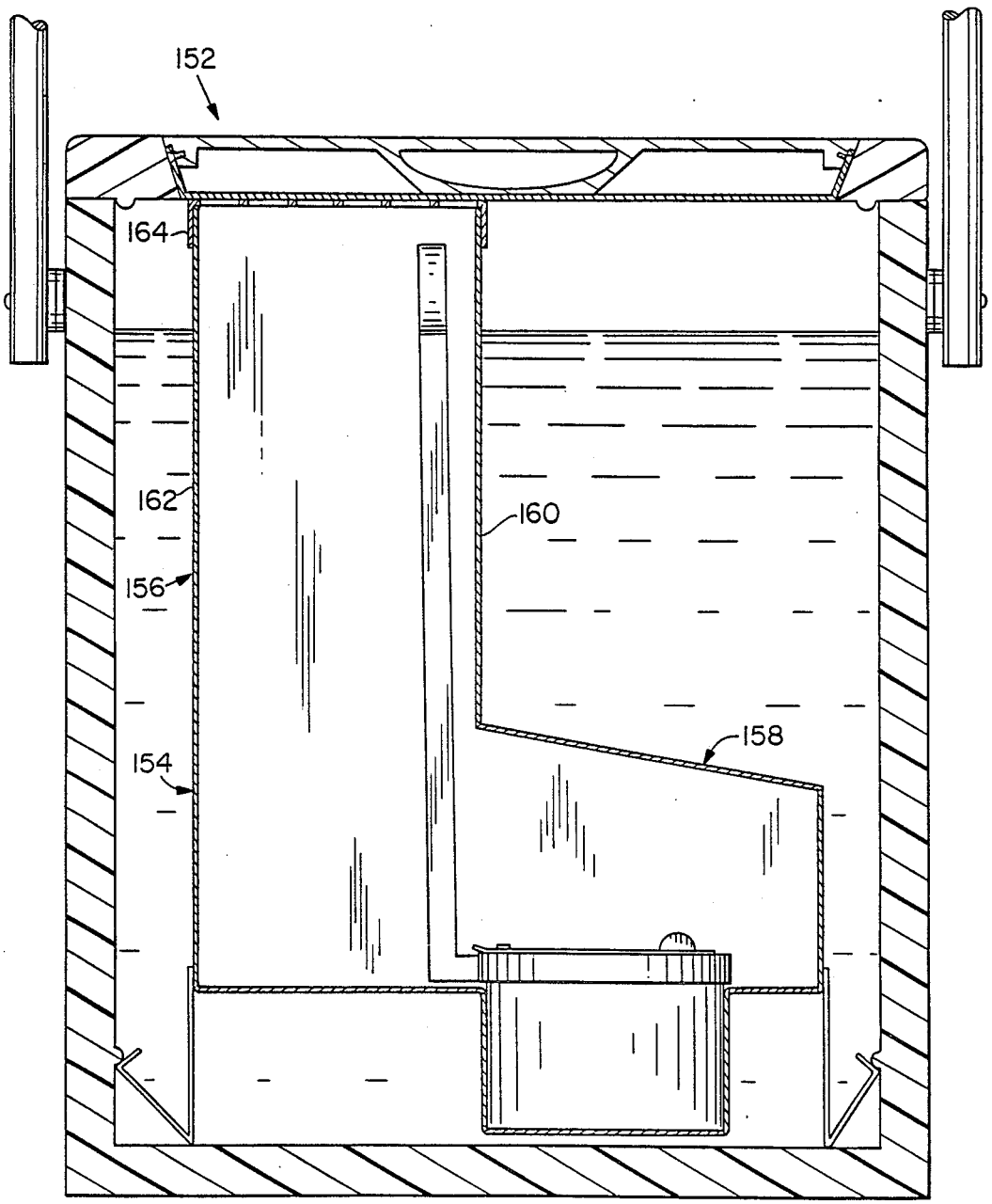
FIG. 9 is a cross-sectional view of an alternative embodiment of the invention including a submersible heating and cooling source having a single conduit.

Shown in FIG. 9 is a versatile heater/cooler 152 similar to heater/cooler 2, but includes a H/C source 154 having only one conduit 156 rather than two. The only fluid passage into or out of the transverse body 158 is by way of conduit 156. When combustion gases rise upwardly through conduit 156, they travel along the hottest wall 160. Air to support combustion passes downwardly through the conduit 156, but close to the relatively cooler wall 162. A perforated grate cap 164 covers the open entrance to conduit 156 in a similar manner as grate cap 112 of the preferred embodiment.

Figures 10, 11:
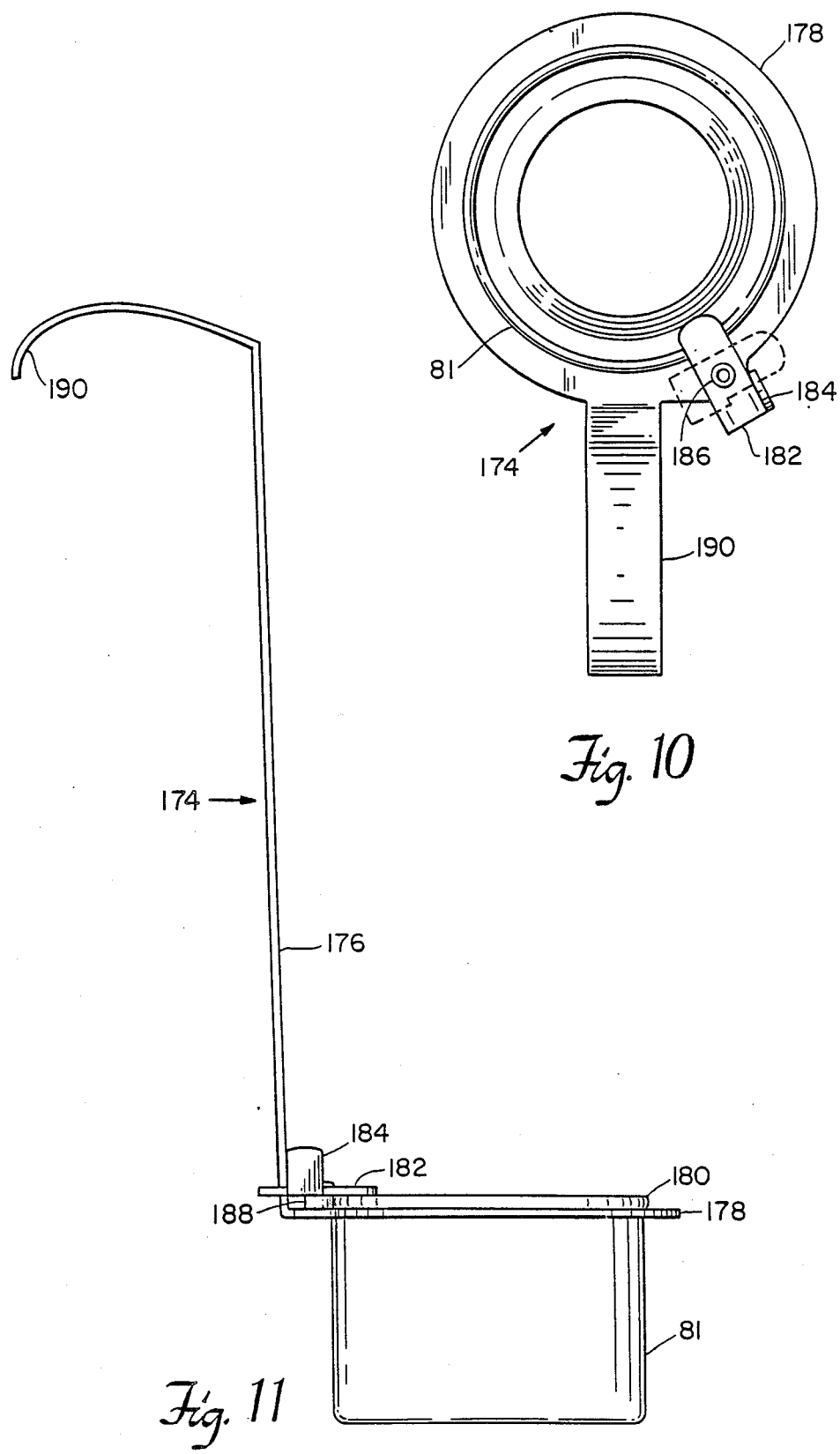
FIG. 10 is a top view of an alternative fuel holding arm.
FIG. 11 is a side elevation view of the fuel holding arm of FIG. 10.

Shown in FIG. 10 and 11, is an alternative fuel holding arm 174 comprising a shaft 176 connected at an angle to a flat ring-shaped holder 178. The holder includes an aperture which receives a close-fitting conventional fuel can 81 of the same type as can 80. A protruding annular top edge 180 of the can prevents the latter from sliding through the holder 178.

Pivotally supported on holder 178 is a latch 182 having a thumb handle 184 comprising a tab extending perpendicularly from the latch. The latch 182 and holder 178, each have a small hole for receiving a rivet 186 which pivotally holds them together. The rivet passes through a spacing washer 188 positioned between the latch and holder.

Thus connected, a user can press his thumb against the thumb handle 184 to move the latch between a locked position and a release position. In the locked position, the latch holds the top of the can and positively prevents the can from coming out of the holder.

An upper end portion of shaft 176 is bent to form a handle 190.

The advantages of fuel holding arm 174 include the added safety of the latch 182 for preventing accidental detachment of the fuel can. Flat holder 178 allows the can to be placed in a deeper fuel well.

The arm 174 can be stamped out of a single piece of flat stock and bent into the described shape. Thus, the arm is simple and inexpensive to produce.

Instead of using the fuel holding arm to remove and replace the fuel can, alternative methods can be used requiring minor modifications of the H/C source. One method (not shown) is to enlarge the roof above the fuel can and incorporate a removable hatch on the roof. The hatch may be a press-fitted type or a screw-on type. Removal and replacement of the fuel can would then be done through the open roof hatch. The hatch would, of course, be closed during operation of the H/C source.

A second alternative method (not shown) of replacing the fuel can in the H/C source is to make the fuel well removable from the transverse body. This can be done by constructing the well as a screw-on item. An upper portion of the well could be encircled by a male thread to mate with a female thread within an annular aperture in the floor of the transverse body. The fuel can could then be replaced by unscrewing the fuel well from the H/C source.

An embodiment of the invention (not shown) can be designed to use two or more cans of fuel simultaneously for faster heating. This can be achieved by widening the walls 60, 56, 68, 64, 70, 74, of H/C source 46, so that one or more fuel wells can be added. The wells can be positioned side-by-side aligned in parallel with the longitudinal axis of the chest.

While the above description contains many specificities, these should not be construed as limitations on the scope of the invention, but rather as exemplifications of preferred embodiments thereof. Those skilled in the art will envision other possible variations that are within its scope. Accordingly, the scope of the invention should be determined not by the embodiments illustrated, but by the appended claims and their legal equivalents.

What is claimed is:

1. A portable temperature conditioning apparatus comprising:
    a container having a plurality of walls defining a hollow interior, the walls having insulating means for inhibiting the transfer of heat through the walls, the walls including a lid having a longitudinal axis and a portion having an edge defining a limb port of a size suitable for insertion of a user's limb through the port and into the interior of the container, the edge being substantially curved in order to comfortably surround the limb;
    means for producing a temperature condition within the container;
    a pair of U-shaped carrying handles, each handle having a pair of legs wherein each leg is pivotally connected to the container such that each handle is movable between an erect position and a lower position; and
    means for retaining the handles in an erect position so that together the handles can support broad surfaced items above the container to aid the user.

2. The apparatus as defined in claim 1, further comprising a limb port cover for removably closing the port when the latter is not in use and at least one latch holding the limb port cover in place so that the cover can not ordinarily be removed from the port by the force of gravity when the lid is in an abnormal position.

3. The apparatus as defined in claim 1, further comprising a self-adjusting shield connected to the port edge portion, the shield including a corolla having a plurality of resilient petals positioned to surround and yieldingly contact a limb passing through the port so that the shield resists the passage of air through the port.

4. The apparatus as defined in claim 1, further comprising the lid having a second limb port positioned such that the alignment of the two limb ports is substantially parallel with the longitudinal axis of the lid so that two limbs of a user can conveniently be simultaneously inserted in the container.

5. The apparatus as defined in claim 4, further comprising the lid having a closable vent port for fluid communication between the interior of the container and the outside of the container, the vent port being positioned approximately equidistant from each limb port.

6. A portable temperature conditioning apparatus comprising:
  a first conduit having a hollow interior and upper and lower end portions wherein the upper end portion includes an opening for fluid communication between the conduit interior and the outside atmosphere;
  a second conduit having a hollow interior and upper and lower end portions wherein the upper end portion includes an opening for fluid communication between the second conduit interior and the outside atmosphere;
  a hollow cylindrical fuel well positioned below the lower end portions of both conduits for containing fuel; and
  connecting means for connecting the well in fluid communication with the interiors of the conduits wherein the conduits the well and the connecting means form a substantially Y-shaped configuration having a plurality of hot exterior surfaces when the fuel is undergoing combustion so that when the Y-shape is closely enclosed by a container containing fluid the hot surfaces together with inner surfaces of the container define openings on each side of the well and between the conduits for enhancing heat transfer by convectional circulation through the openings.

7. The apparatus as defined in claim 6, further comprising a fuel holding arm for placing and removing a fuel can by passing the can through one of the conduits and inserting the can into the fuel well, the arm comprising:
  a shaft having a lower end portion; and
  embracing means for detachably connecting the shaft lower end portion laterally to an upper end portion of the can by embracing the same.

8. The apparatus as defined in claim 6, further comprising the body having a lighting port for igniting the fuel and a removable cap sealing the port in a fluid tight manner.

9. The apparatus as defined in claim 9, further comprising the combination being enclosed by a container having a longitudinal axis and including a plurality of walls having insulating means for inhibiting the transfer of heat through the walls, the walls including a lid and means for allowing fluid communication between the conduits and the exterior of the container, the walls defining a rectangular sided interior wherein the Y-shape spans the interior at a position perpendicular to the longitudinal axis such that the openings defined by the Y-shape allow convectional circulation of fluid in the container wherein the fluid circulates through the openings for heat transfer.

10. The apparatus as defined in claim 6, wherein the upper end portion openings of both conduits are normally at about the same height and the connecting means together with the lower end portion of the first conduit form a first conduit passage and the connecting means together with the lower end portion of the second conduit form a second conduit passage which is relatively lower and smaller in area than the first passage, the fuel well being relatively lower than both passages so that during combustion of fuel the combination produces a draft moving upward in the first conduit and downward in the second conduit.

11. The apparatus as defined in claim 6, wherein the connecting means includes a body having a roof and a floor which define respective upper and lower limits of a chamber positioned below the upper end portions of the conduits, the roof being generally sloped upward toward the first conduit such that the vertical distance within the chamber between the floor and the roof generally increases as the distance toward the first conduit decreases, the well having an entranced through the chamber floor and the well being positioned directly below the slope of the roof such that when a fuel source is introduced into the chamber by way of the first conduit the sloped roof guides the fuel source downward toward the well entrance to a position for entry into the well.

12. The apparatus as defined in claim 11, wherein the fuel source is a can containing semi-solid fuel.

13. The portable temperature conditioning apparatus as defined in claim 6, wherein a cross-sectional area taken perpendicularly through a longitudinal axis of the first conduit is substantially larger than a cross-sectional area taken perpendicularly through a longitudinal axis of the second conduit for greater heat transfer from combustion gases and efficient combustion.

14. A portable temperature conditioning apparatus comprising:
  a conduit having a hollow interior and upper and lower end portions wherein the upper end portion includes an opening for fluid communication between the conduit interior and the outside atmosphere, the conduit having an air passage portion and a combustion gas passage portion;
  a body having a roof and a floor which define respective upper and lower limits of a combustion chamber positioned below the upper end portion of the conduit and the body being connected to the lower end portion of the conduit for fluid communication between the chamber and the conduit interior;
  a hollow fuel well extending downward from the body for receiving a fuel source; and
  means for sealing the combination such that the well and body including the combustion chamber and roof are fluid tight and submergible in a liquid for heating the latter by combustion of fuel.

15. The portable temperature conditioning apparatus as defined in claim 14, wherein the fuel entry means includes the roof being sloped generally upward toward the conduit such that the vertical distance within the chamber between the floor and the roof generally increases as the distance toward the conduit decreases, the well being positioned directly below the slope such that when the fuel source is introduced in the apparatus by way of the conduit the sloped roof guides the fuel source downward toward the well entrance for entry into the well wherein the slope cooperates in producing a combustion supporting draft by guiding combustion gases to the combustion gas passage portion of the conduit thereby drawing atmospheric air down the air passage portion.

16. A portable temperature conditioning apparatus comprising:
- a conduit having a hollow interior and upper and lower end portions wherein the upper end portion includes an opening for fluid communication between the conduit interior and the outside atmosphere;
- connecting means for connecting a fuel source in fluid communication with the interior of the conduit for supporting combustion of fuel;
- a container having a plurality of walls enclosing the conduit and connecting means, the walls having insulating means for inhibiting the transfer of heat through the walls, the container having an opening for allowing fluid communication between the conduit interior and the exterior of the container; and
- an openable cover positioned across the container opening thereby inhibiting the passage of air therethrough, the cover having a bottom surface positioned at the conduit opening for blocking the same thereby preventing combustion of fuel.

17. The apparatus as defined in claim 16, wherein the cover includes means for forming a temperature barrier across the container opening and across the conduit opening.

18. The apparatus as defined in claim 16, wherein the container opening is a vent port defined by an openable lid which forms an upper wall of the container.

19. The apparatus as defined in claim 16, further comprising the connecting means having a plurality of legs extending therefrom, at least one of the legs including means for anchoring to the container to prevent the conduit and fuel source from floating when the container contains a liquid.

20. A portable combustion apparatus comprising:
- a first conduit having a hollow interior and upper and lower end portions wherein the upper end portions includes an opening for fluid communication between the conduit interior and the outside atmosphere;
- a second conduit having a hollow interior and upper and lower end portions wherein the upper end portion includes an opening for fluid communication between the second conduit interior and the outside atmosphere;
- a body defining a combustion chamber and the body being connected with the lower end portions of the first and second conduits such that the chamber is in fluid communication with the interiors of the conduits, the body having a roof for transferring heat to an environment in which the body can be submerged; and
- a hollow well extending downward from the body, the well being in fluid communication with the combustion chamber and with the interiors of the first and second conduits.

21. The apparatus as defined in claim 20, wherein the roof includes an underside positioned directly over the chamber wherein the underside is sloped to extend in a downward direction to a lateral portion of the chamber.

22. A heater for heating liquid comprising:
- a first conduit having a hollow interior and upper and lower end portions wherein the upper end portion includes an opening for fluid communication between the conduit interior and the outside atmosphere;
- a second conduit having a hollow interior and upper and lower end portions wherein the upper end portion includes an opening for fluid communication between the second conduit interior and the outside atmosphere;
- a body defining at least a portion of a combustion chamber, the body being connected with the lower end portions of the first and second conduits such that the chamber is in fluid communication with the interiors of the conduits, the body having a roof for transferring heat to a liquid environment in which the body can be submerged, the roof having an underside positioned directly over the chamber wherein the underside is sloped to extend in a downward direction to a lateral portion of the chamber; and
- a hollow well extending downward from the body; the well being in fluid communication with the combustion chamber and with the interiors of the first and second conduits.

23. A heater for heating liquid comprising:
- a first conduit having a hollow interior and upper and lower end portions wherein the upper end portion includes an opening for fluid communication between the conduit interior and the outside atmosphere;
- a second conduit having a hollow interior and upper and lower end portions wherein the upper end portion includes an opening for fluid communication between the second conduit interior and the outside atmosphere; and
- a body defining at least a portion of a combustion chamber, the body being connected with the lower end portions of the first and second conduits such that the chamber is in fluid communication with the interiors of the conduits, the body having a roof for transferring heat to a liquid environment in which the body can be submerged, the roof having an underside positioned directly over the chamber wherein the underside is sloped to extend in a downward direction to a lateral portion of the chamber.

* * * * *